United States Patent [19]

Battles et al.

[11] 4,409,821
[45] Oct. 18, 1983

[54] SOLID PROPELLANT MEASUREMENT SYSTEM

[75] Inventors: James W. Battles; H. Bernard Mathes, both of Ridgecrest, Calif.

[73] Assignee: The United States of America as represented by the Secretary of the Navy, Washington, D.C.

[21] Appl. No.: 291,757

[22] Filed: Aug. 10, 1981

[51] Int. Cl.³ .............................................. G01L 5/13
[52] U.S. Cl. .................................................. 73/116
[58] Field of Search .............. 73/116, 290 R; 60/234, 60/253, 254; 403/342

[56] References Cited

U.S. PATENT DOCUMENTS

| | | | |
|---|---|---|---|
| 3,533,485 | 10/1970 | Buffum, Jr. et al. | 181/0.5 |
| 3,589,177 | 5/1971 | Merlo | 73/116 |
| 3,788,126 | 1/1974 | Price et al. | 73/35 |
| 4,157,163 | 6/1979 | Pinto et al. | 403/342 |
| 4,210,023 | 7/1980 | Sakamoto et al. | 73/290 R |

OTHER PUBLICATIONS

James E. Crump, H. Bernard Mathes, Jr., High Frequency T-Burner for Solid Propellant Testing, Jul. 1977, vol. 2, pp. 33–37.

Primary Examiner—E. R. Kazenske
Assistant Examiner—Brian Tumm
Attorney, Agent, or Firm—R. F. Beers; W. Thom Skeer

[57] ABSTRACT

An apparatus for measuring the burning rate of solid propellants utilizes a homodyne radar to illuminate the propellant grain from a non-burning surface to obtain a distance measurement of the dimensions of the burning mass.

8 Claims, 2 Drawing Figures

SOLID PROPELLANT MEASUREMENT SYSTEM

BACKGROUND OF THE INVENTION

1. Field of the Invention

This invention pertains to the measurement of solid propellant fuels. More particularly, this invention pertains to an apparatus for measuring the burning rate of solid propellants in a controlled environment. By way of further characterization, the invention will be described as it relates to an apparatus for the determination of the burning rate of solid propellants.

2. Description of the Prior Art

The measurement of burning characteristics of solid propellants is a vital part of the design of rocket motors. In the past, the burning rates have been measured by burning carefully machined samples of the propellant in a tube and using the volume of the propellant to tune the tube such that acoustic measurements are indicative of the dimensions of the burning sample. An example of this technique is illustrated in U.S. Pat. No. 3,533,485 issued on Oct. 13, 1970 to Frank G. Buffum, Jr. et al. for "Method and Apparatus for Determining the Accoustics of Rocket Motor Chambers". It is also known to use electrical energies to tune the combustion chamber where the propellant is a dielectric in a waveguide system which is tuned by the consumption of the burning propellant.

SUMMARY OF THE INVENTION

This invention determines the burning rate of a solid propellant by the use of a homodyne radar which is coupled to the back of the propellant sample and impedance matched thereto such that the exact position of the burning face may be determined from microwave signals reflected through the sample to the homodyne detection system. This simple and direct method overcomes many of the frustrations of the prior art methods by providing an exact, real-time, measurement of the burning propellant sample such that the burning rate may be acurately determined. Further, the invention uses existing hardware such that expensive test facilities are not made obsolescent thereby. Additionally, the system employs conventional propellant grain shapes such that comparison with past results may be easily performed.

It is, accordingly, an object of this invention to provide an apparatus for measuring propellant fuels.

A further object of this invention is the provision of an apparatus for the measurement of burning rate with a higher accuracy than heretofore was available.

Another object of this invention is the provision of an apparatus which permits a high speed of measurement.

These and other objects of the invention will become apparent to those versed in the art by reference to the appended descriptions, drawings, and claims.

DESCRIPTION OF THE PREFERRED EMBODIMENT

Figure 1:
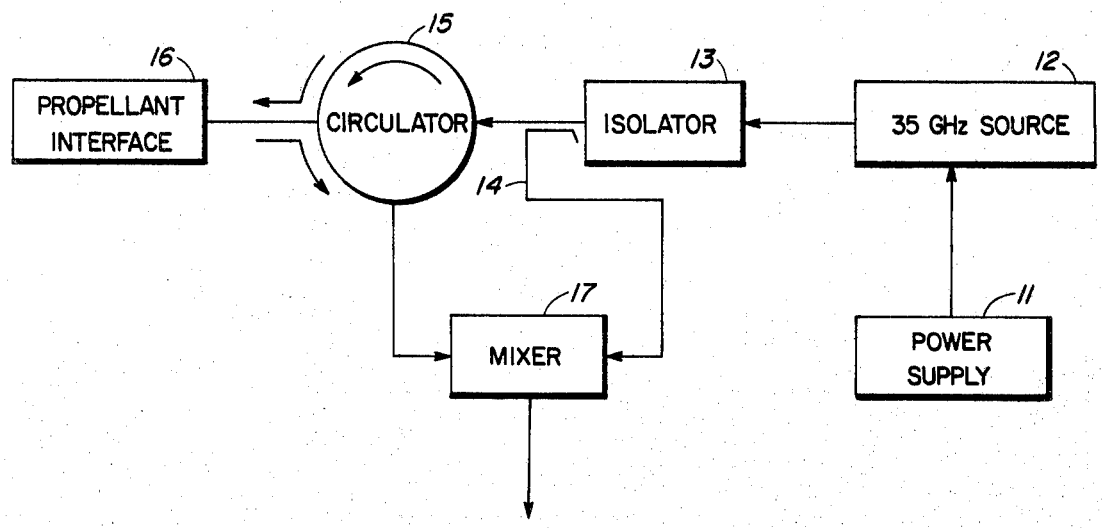
FIG. 1 is a block diagram of the circuitry according to the invention.

Referring to FIG. 1, a conventional power supply 11 provides operating electrical potential for a thirty-five gigahertz Gunn source 12. The output of the microwave source 12 is fed, via isolator 13 to a circulator 15. Isolator 13 protects gun source 12 from reflected microwave energies which would possibly interfere with the output thereof. Circulator 15 is a conventional electronic microwave device which feeds microwave energy in the direction of the arrow, hence its name. The output of circulator 15 is fed to a propellant interface system 16, to be described in greater detail herein.

Reflected energies from propellant interface 16 provide a real-time measurement of the position of the burning face of the propellant sample. This reflected energy is transmitted by the circulator 15 to the input of a mixer circuit 17. Mixer circuit 17 obtains a homodyne input from a directional coupler 14 such that the output thereof is a homodyne mixture which may be processed, in a conventional fashion, to provide a distance measurement from the back of the propellant sample to the burning face thereof.

Figure 2:
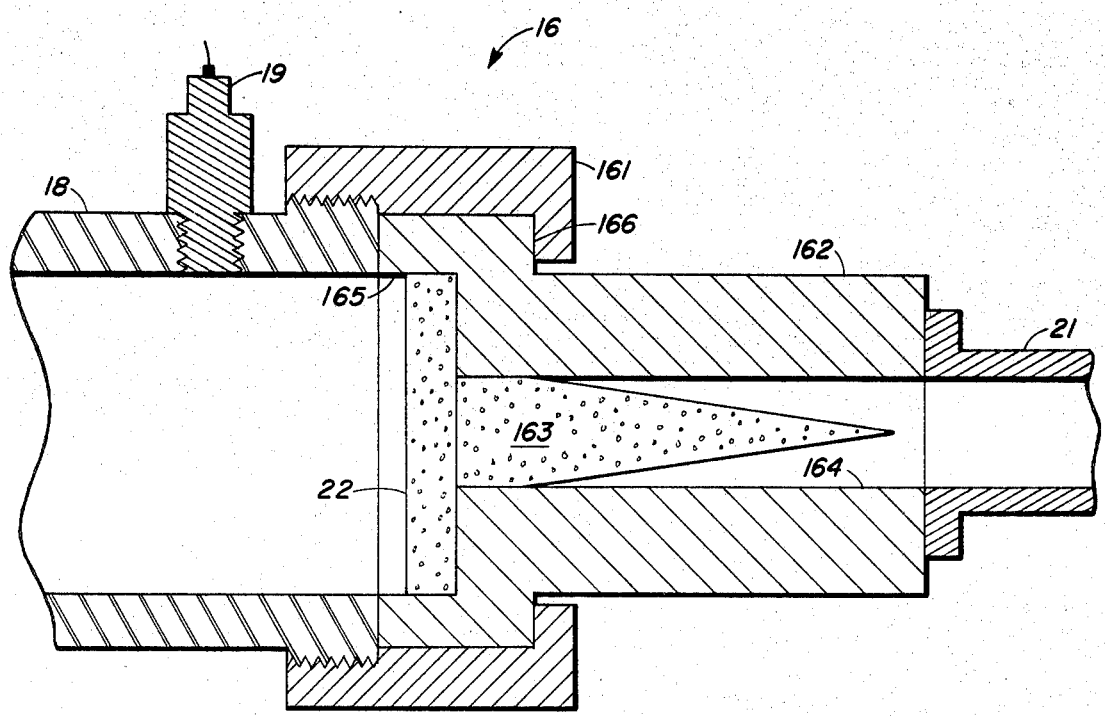
FIG. 2 is a sectional view of the propellant holder and microwave coupler utilized in the invention.

Referring to FIG. 2, a cross section of propellant grain interface 16 is illustrated. The locking ring 161 slidably extends over a cylindrical body portion 162. A matching dielectric transition stub 163 closes an axial bore 164 which mates with a waveguide 21. Waveguide 21 functions as a source of millimeter wavelength microwave energy. A cylindrical end portion 165 has space to receive a propellant sample 22 of standard dimensions. Cylindrical end portion 165 joins cylindrical body portion 162 at a shoulder indicated at 166. The inner surface of locking ring 161 is threaded and is threadably engaged by the end of a gas load device such as T-burner 18 in the conventional fashion. T-burner 18 has provision for mounting a pressure transducer 19 in a well-known manner.

Bore 164 of sample holder 16 interfaces with waveguide 21 to provide a continuous transmission path. As is conventional in the microwave plumbing arts, waveguide 21 may be fitted to cylindrical portion 162 by a conventional choke joint not shown.

In operation, sample 22 is mounted in sample holder 16 and the holder attached to T-burner 18. The microwave energy output from waveguide 21 is coupled to sample 22 by the impedance matching action of stub 163 in the well understood fashion. Propellant 22 is then ignited and allowed to burn producing the energy associated with that combustion. As the face of the propellant sample is consumed, a real-time signal indicative of its position is outputted from mixer 17, FIG. 1.

This signal may be processed to give the data useful in calculation of parameters of combustion responsive to acoustic environmental changes as monitored by transducer 19.

Although described in a test environment, it is obvious that a similar technique could be employed in other applications where a solid propellant is being consumed. Thus if used with a rocket powered vehicle the output of the apparatus may be used to indicate fuel consumption rate, fuel remaining, or other operational parameters.

Cylindrical housing 162 and locking ring 161 are made of conventional materials such as stainless steel. Similarly, the tuning stub 163 may be fabricated from conventional dielectrics. Likewise, the circuit components are well known, off-the-shelf, electronic components. Choices among various manufacturers and designs of components is within the purview of one skilled in the art, recognizing the customary engineering trade-offs.

The foregoing description taken together with the appended claims constitutes a disclosure such as to enable one versed in the instrumentation and machine arts to make and use the invention. Further, this disclosure constitutes a meritorious advance in the instrumentation arts unobvious to the worker not having the benefit of these teachings.

What is claimed is:

1. Apparatus for measuring propellant combustion comprising:
   a propellant grain holder;
   a propellant gas load connected to said propellant grain holder;
   a source of millimeter wavelength microwave energy having a predetermined electrical output impedance;
   coupling means connected between said source of microwave energy and said propellant grain holder, said coupling means being configured to match the electrical output impedance of said source of millimeter wavelength microwave energy to the impedance of said propellant grain holder; and
   circuit means connected to said source of millimeter wavelength microwave energy for comparing the millimeter wavelength microwave energy coupled to said propellant grain holder and millimeter wavelength energy reflected from a propellant grain held in said propellant grain holder.

2. An apparatus according to claim 1 in which said propellant grain holder includes:
   a cylindrical end configured to accept and position a propellant sample within;
   a cylindrical body portion attached to said cylindrical end so as to provide a shoulder at the junction thereof;
   a locking ring having an aperture to slidingly fit over said cylindrical body portion and an enlarged end internally threaded to fit over said cylindrical end to engage said propellant gas load so as to urge said cylindrical end thereagainst in a gas-tight connection.

3. An apparatus according to claim 1 wherein said gas load is a T-burner.

4. An apparatus according to claim 3 wherein said gas load includes a pressure transducer.

5. An apparatus according to claim 1 wherein said gas load includes a pressure transducer.

6. An apparatus according to claim 1 wherein said source of microwave energy is a millimeter waveguide.

7. An apparatus according to claim 1 in which said coupling means is a wedge of dielectric material mounted in said propellant grain holder with its base adjacent said propellant grain and its apex adjacent said source of millimeter wavelength microwave energy.

8. An apparatus according to claim 1 wherein said circuit means includes:
   an isolator for electrically isolating the circuit means from an external source of microwave energy;
   a circulator having an input connected to said isolator and an input-output connected to said source of millimeter wavelength microwave energy and an output;
   a directional coupler connected to said isolator for bleeding-off a portion of the output therefrom; and
   a mixer having a first input connected to said directional coupler, a second input connected to the output of said circulator and having an output for producing a homodyne output signal indicative of the position of the face of the propellant grain in said propellant grain holder.

* * * * *